US011497810B2

(12) United States Patent
Garcia Gonzalez et al.

(10) Patent No.: US 11,497,810 B2
(45) Date of Patent: Nov. 15, 2022

(54) SYSTEM FOR ADMINISTERING BIOLOGICALLY ACTIVE SUBSTANCES PRODUCED BY FOAMING TECHNIQUES USING COMPRESSED GASES OR SUPERCRITICAL FLUIDS

(71) Applicant: UNIVERSIDADE DE SANTIAGO DE COMPOSTELA, Santiago de Compostela (ES)

(72) Inventors: Carlos Garcia Gonzalez, Santiago de Compostela (ES); Luis A Diaz Gomez, Santiago de Compostela (ES); Carmen Alvarez Lorenzo, Santiago de Compostela (ES); Angel J Concheiro Nine, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 0 days.

(21) Appl. No.: 15/746,726

(22) PCT Filed: Jul. 12, 2016

(86) PCT No.: PCT/ES2016/070528
§ 371 (c)(1),
(2) Date: Jan. 22, 2018

(87) PCT Pub. No.: WO2017/013288
PCT Pub. Date: Jan. 26, 2017

(65) Prior Publication Data
US 2018/0236086 A1    Aug. 23, 2018

(30) Foreign Application Priority Data

Jul. 23, 2015    (ES) .................... P201531087

(51) Int. Cl.
| A61K 47/34 | (2017.01) |
| A61K 47/36 | (2006.01) |
| A61K 47/26 | (2006.01) |
| A61L 27/18 | (2006.01) |
| C08L 3/02  | (2006.01) |
| C08L 67/04 | (2006.01) |

(52) U.S. Cl.
CPC .............. *A61K 47/34* (2013.01); *A61K 47/26* (2013.01); *A61K 47/36* (2013.01); *A61L 27/18* (2013.01); *C08L 3/02* (2013.01); *C08L 67/04* (2013.01); *C08L 2203/02* (2013.01)

(58) Field of Classification Search
None
See application file for complete search history.

(56) References Cited

U.S. PATENT DOCUMENTS

| 5,004,602 | A   | 4/1991  | Hutchinson |
| 6,013,853 | A   | 1/2000  | Athanasiou et al. |
| 2002/0155145 | A1* | 10/2002 | Howdle ................. A61K 6/033 424/424 |
| 2005/0079470 | A1* | 4/2005  | Rutherford ............ A61K 6/033 433/226 |
| 2011/0034418 | A1  | 2/2011  | Beltz et al. |

FOREIGN PATENT DOCUMENTS

| WO | 9109079 A1 | 6/1991 |
| WO | 0214403 A2 | 2/2002 |

OTHER PUBLICATIONS

Sheridan et al., "Bioabsorbable polymer scaffolds for tissue engineering capable of sustained growth factor delivery", J Controlled Release 64: 91-102 (2000) (Year: 2000).*
Koenig and Huang, "Biodegradable blends and composites of polycaprolactone and starch derivatives", Polymer 36: 1877-1882 (1995) (Year: 1995).*
Robert Shanks and Ing Kong (2012). Thermoplastic Starch, Thermoplastic Elastomers, Prof. Adel El-Sonbati (Ed.), ISBN: 978-953-51-0346-2, InTech, Available from: http://www.intechopen.com/books/thermoplasticelastomers/thermoplastic-starch, p. 95-116. (Year: 2012).*
Vroman, I; et al. "Biodegradable Polymers" Materials 2009, 2, 307-344. (Year: 2009).*
Singh, L. et al. "Generation of porous microcellular 85/15 Poly . . . " Biomaterials, 2004, 25(13), 2611-2617. (Year: 2004).*
Geusens, P.; et al. "NSAIDs and fracture healing" Current Opinion Rheumatology, v. 25, No. 4, Jul. 2013, 524-531.*
International Search Report dated Oct. 3, 2016 re: Application No. PCT/ES2016/070528; pp. 1-5; citing: Sheridan et al., US 2002155145 A1, Zhao-Li et al., WO 9109079 A1, U.S. Pat. No. 5,004,602 A, US 2011034418 A1, WO 0214403 A2 and U.S. Pat. No. 6,013,853 A.
Amir A. Zadpoor "Bone tissue regeneration: the role of scaffold geometry" Biomaterials Science; Royal Society of Chemistry; Oct. 30, 2014; vol. 3; pp. 231-245.

(Continued)

*Primary Examiner* — Erin E Hirt
(74) *Attorney, Agent, or Firm* — Cantor Colburn LLP (57) ABSTRACT

A system for administering biologically active substances produced by foaming techniques using compressed gases or supercritical fluids relates to a porous system containing biologically active substances. The system includes a polymer matrix of poly(D,L-lactic-co-glycolic acid) or a polymer mixture containing poly(D,L-lactic-co-glycolic acid) of an intrinsic viscosity of less than 0.5 dL/g with other biodegradable synthetic or semisynthetic polyesters, a release-regulating component (starch and derivatives), and at least one biologically active substance. The matrix is biodegradable with a solid or semisolid consistency and a homogeneous appearance. A method for producing these systems using foaming with compressed fluids, and the use for the production of implants and scaffolds having this system are also disclosed. Optionally, a porogenic agent can be used for the formation of macropores by thermal decomposition.

2 Claims, 5 Drawing Sheets

(56) References Cited

OTHER PUBLICATIONS

Hirenkumar K. Makadia et al., "Poly lactic-co-glicolic acid (PLGA) as biodegradable controlled drug delivery carrier" Polymer; Sep. 1, 2011; vol. 3; No. 3; pp. 1377-1397.

James M. Anderson et al., "Biodegradation and biocompatibility of PLA and PLGA microspheres" Advanced Drug Delivery Reviews; 2012; vol. 64; pp. 72-82.

K. Rezwan et al., "Boccaccini AR, Biodegradable and bioactive porous polymer/inorganic composite scaffolds for bone tissue engineering" Biomaterials; 2006; vol. 27; pp. 3413-3431.

M. H. Sheridan et al., "Bioabsorbable polymer scaffolds for tissue engineering capable of sustained growth factor delivery" Journal of Control Release; 2000; vol. 64, No. 1-3; pp. 91-102.

Ning Wang et al., "Influence of formamide and water on the properties of thermoplastic starch/poly(lactic acid) blends" Carbohydrate Polymers; 2008; vol. 71; pp. 109-118.

Ramaswamy Mani et al., "Properties of injection moulded blends of starch and modified biodegradable polyesters" European Polymer Journal; 2001; vol. 37; pp. 515-526.

Richard A. Graves et al., "Effect of different ratios of high and low molecular weight PLGA blend on the characteristics of pentamidine microcapsules" International Journal of Pharmaceutics; 2004; vol. 270; pp. 251-262.

Sang-Soo Kim et al., "A poly(lactide-co-glycolide)/hydroxyapatite composite scaffold with enhanced osteoconductivity" Journal of Biomedical Materials Research Part A; Oct. 27, 2006; vol. 80A; No. 1; pp. 206-215.

Vassilis Karageorgiou et al., "Porosity of 3D biomaterial scaffolds and osteogenesis" Biomaterials; 2006; vol. 26; pp. 5474-5491.

Zhao-Li Mou, et al. "Preparation of porous PLGA/HA/collagen scaffolds with supercritical CO2 and application in osteoblast cell culture" Journal of Supecritical Fluids, Journal of Supercritical Fluids; 2011; vol. 58; No. 3; pp. 398-406.

Agata Przekora et al. "In vitro evaulation of the risk of inflammatory response after chitosan/HA and chitosan/B-1,3-glucan/HA bone scaffold implantation", Materials Science and Engineering C vol. 61, 2016, pp. 355-361, www.elsevier.com/locate/msec.

Alexandra Wibberley et al. "Dual, but not selective, COX-1 and COX-2 inhibitors, attenuate acetic acid-evoked bladder irritation in the anaesthetised female cat", British Journal of Pharmacology, 2006, vol. 148, pp. 154-161.

Amir A. Zadpoor "Bone tissue regeneration: the role of scaffold geometry", Biomaterials Science, Royal Society of Chemistry, 2014, pp. 1-15.

Ceclilia Romagnoli et al. "Drug delivery using composite scaffolds in the context of bone tissue engineering", Mini Review, Clinical Cases in Mineral and Bone Metabolism, 2013, vol. 10, No. 3, pp. 155-161.

Herve Nyangoga et al. "A non-steroidal anti-inflammatory drug (ketoprofen) does not delay B-TCP bone graft healing", Acta Biomaterialia, 2010, vol. 6, pp. 3310-3317.

Huub J L van der Heide et al. "No effect of ketoprofen and meloxiam on bone graft ingrowth", Acta Orthopaedica, 2008, vol. 79, No. 4, pp. 548-554.

Ippokratis Pountos et al. "Do Nonsteroidal Anti-Inflammatory Drugs Affect Bone Healing? A Critical Analysis", The Scientific World Journal, vol. 2012, ArticleID 606404, pp. 1-15.

L. Diaz-Gomez et al. "Low viscosity-PLGA scaffolds by compressed CO2 foaming for growth factor delivery", RSC Advances, Royal Society of Chemistry, Jul. 18, 2016, vol. 6, pp. 70510-70519.

Nathaniel M. Vacanti et al. "Localized Delivery of Dexamethasone from Elecrospun Fibers Reduces the Foreign Body Response", BioMacromolecules, American Chemical Society, 2012, vol. 13, pp. 3031-3038.

Rukmani Sridharan et al. "Biomaterial based modulation of macrophage polarization: a review and suggested design principles" Materials Today, Elsevier, vol. 00, No. 00, Jan. 2015.

\* cited by examiner

SYSTEM FOR ADMINISTERING BIOLOGICALLY ACTIVE SUBSTANCES PRODUCED BY FOAMING TECHNIQUES USING COMPRESSED GASES OR SUPERCRITICAL FLUIDS

TECHNICAL FIELD

The disclosure is aimed at a system for administering biologically active substances. More specifically, the system comprises a matrix comprising poly(D,L-lactic-co-glycolic acid) (PLGA). The disclosure is also aimed at a method for producing said systems; more specifically the method comprises a stage of foaming using a compressed gas or supercritical fluid. Alternatively, a porogenic agent is incorporated to form macropores by thermal decomposition. The disclosure is also aimed at the use of these systems.

BACKGROUND

Regenerative medicine requires synthetic implants that can act as three-dimensional scaffolds and that actively participate in tissue regeneration, acting as delivery systems of active substances and guiding tissue growth.

Polyesters are a group of biodegradable polymers widely used to build scaffolds. One of the most common polyesters is poly(D,L-lactic-co-glycolic acid) (PLGA), which degrades by hydrolysis of their ester bonds resulting in oligomers and monomers. The physical and mechanical properties and resistance to degradation of this polymer can be tuned by adjusting the monomers ratio, the molecular weight and the degree of crystallinity (Makadia H K, Siegel S J, *Poly lactic-co-glicolic acid (PLGA) as biodegradable controlled drug delivery carrier. Polym* 3, 1377-1397, 2011). It has been reported that PLGA microspheres have a variable degradation time from 8 to 35 weeks, depending particularly on the lactic:glycolic ratio of the PLGA (Anderson J M, Shive M S, *Biodegradation and biocompatibility of PLA and PLGA microspheres. Adv Drug Del Rev* 64, 72-82, 2012). This variability of degradation times allows the degradation kinetics of the scaffold to be tuned to the growth rate of the neo-tissue, which is essential for the proper functioning of the scaffolding and the regeneration performance.

The use of PLGA with low inherent viscosity is particularly suitable for the regeneration of bone tissue, as the degradation time is between 8 and 10 weeks. However, it has been reported that the preparation of a porous matrix of PLGA with low inherent viscosity (0.2 dL/g) by foaming with $CO_2$ resulted in a scaffold with inadequate consistency, since the matrix underwent such an excessive expansion during foaming that the scaffold lost its physical and mechanical integrity and, therefore, resulted in a scaffold that is not useful (Sheridan M H, Shea L D, Peters M C, Mooney D J, *Bioabsorbable polymer scaffolds for tissue engineering capable of sustained growth factor delivery. J Control Release* 2000, 64 (1-3), 91-102).

In addition, scaffolds based on PLGA with low inherent viscosity have poor ability to control the release of biologically active substances which are incorporated into the polymer matrix of PLGA (Graves R A, Pamujula S, Moiseyev R, Freeman T h, Bostanian L A, Mandal T K, *Effect of different ratios of high and low molecular weight PLGA blend on the characteristics of pentamidine microcapsules. Int J Pharm* 2004, 270, 251-262).

Furthermore, obtaining dual porosity scaffolds by foaming using compressed gases or supercritical fluids is a technical challenge. Macropores of 200-600 microns are often created by incorporating water-soluble particles such as sodium chloride, sodium bicarbonate, glucose, dextrin or trehalose into the scaffold, which form macropores in the polymer matrix during subsequent leaching. The leaching process has the disadvantages that during washing a significant proportion of the active substances can be lost and that it requires an additional stage of drying the scaffolds, thus lengthening the processing time (Kim S S, Ahn K M, Park M S, Lee J H, Choi C Y, Kim B S, *A poly(lactide-co-glycolide)/hydroxyapatite composite scaffold with enhanced osteoconductivity. J Biomed Mater Res A* 2007, 80A (1), 206-215).

Thus, there remains a need to provide porous matrices based on PLGA with low inherent viscosity with properties that make it useful for the production of scaffolds, and capable of incorporating biologically active substances and release them in a controlled manner over time.

SUMMARY

The authors of the present disclosure have developed a system for administering biologically active substances based on PLGA with an inherent viscosity of less than 0.5 dL/g, which allows the biologically active substances to be released in a controlled manner over time. In addition, the system of the disclosure comprises a biodegradable, porous, homogeneous matrix with a solid or semi-solid consistency, which make it particularly suitable for regenerative medicine and in particular to prepare scaffolds.

Thus, in a first aspect, the disclosure relates to a system for administering biologically active substances comprising a homogeneous and biodegradable matrix with a solid or semi-solid consistency having a porosity higher than 50%, said matrix comprises poly(D, L-lactic-co-glycolic acid) of an inherent viscosity less than 0.5 dL/g, and at least one biologically active substance.

A second aspect of the disclosure relates to a method for obtaining a system for administering biologically active substances comprising a homogeneous and biodegradable matrix with a solid or semi-solid consistency having a porosity higher than 50%, said matrix comprising poly(D, L-lactic-co-glycolic acid) and at least one biologically active substance, comprising:
 a) preparing a physical mixture comprising poly(D,L-lactic-co-glycolic acid) and a biologically active substance and, optionally a porogenic agent;
 b) heating the mixture at a temperature equal to or less than 40° C.,
 c) placing the said mixture in contact with a compressed gas or supercritical fluid at a pressure between 40 and 120 bar and a temperature between 20 and 40° C. during a time period between 5 minutes and 24 hours; and
 d) depressurization at a rate between 2 and 8 bar/min with cooling through the addition of a compressed liquid at a temperature between −196 and 19° C., the liquid being gaseous at 25° C. and 1 atmosphere of pressure.

In a particular embodiment of the second aspect of the disclosure, the poly (D, L-lactic-co-glycolic acid) has an inherent viscosity less than 0.5 dL/g.

A third aspect of the disclosure relates to a system obtained by the method described above.

A fourth and fifth aspect of the disclosure relate to an implant and a scaffold comprising a system as described above, respectively.

A sixth aspect of the disclosure refers to the use of systems of the disclosure, of the implant or of the scaffold of the disclosure, for the production of a medicament. In a particular embodiment, the disclosure is aimed at systems, scaffolds and implants as described above, for the use thereof as a medicament. In another particular embodiment, the medicament is for the treatment of pathological or physiological states in humans or animals. In a more particular embodiment, the medicament is for bone regeneration. In another particular embodiment, the medicament is for cartilage regeneration. In another aspect, the disclosure is aimed at the use of the system as defined above for the preparation of scaffolds for regenerative medicine and tissue engineering.

The scaffold according to the disclosure is suitable as a monolithic implant or as a multiparticulate system for the controlled release of biologically active substances in the application site and the induction of cell differentiation and tissue regeneration. In a particular embodiment, the systems of the disclosure, implants and scaffolds as described above, are part of a monolithic or multiparticulate implant. In a particular embodiment, the system of the disclosure can be obtained as a set of particles or as a monolithic implant for the controlled release in the application site without toxic effects.

DETAILED DESCRIPTION OF THE DISCLOSURE

The disclosure relates to a system for administering biologically active substances, as previously defined, which exhibits characteristics that are particularly suitable for the regeneration of bone and cartilage tissue. Thus, in a first aspect, the disclosure relates to a system for administering biologically active substances comprising an homogeneous and biodegradable matrix with a solid or semi-solid consistency having a porosity higher than 50%, said matrix comprises poly(D, L-lactic-co-glycolic acid) with an inherent viscosity less than 0.5 dL/g, and at least one biologically active substance.

Poly(D,L-lactic-co-glycolic acid) (PLGA) is a biodegradable synthetic polymer of the aliphatic polyester family, in particular it is an alpha-hydroxy acid copolymer of poly (lactic) acid and poly(glycolic) acid. Poly(D,L-lactic-co-glycolic acid) for the present disclosure also includes copolymers of poly(lactic acid) and poly(glycolic acid) having a terminal group selected from hydroxyl, carboxyl and ester. The PLGA of the disclosure has a lactic:glycolic ratio of between 85:15 and 40:60, preferably between 75:25 and 50:50.

PLGA is being given special attention for biomedical applications and has been approved for certain applications by the FDA. PLGA is degraded by the hydrolysis of the ester bonds thereof in the aqueous medium of the body. The physical and mechanical properties and resistance to degradation of this polymer can be tuned by adjusting the monomer ratio, the molecular weight and the degree of crystallinity (Makadia H K, Siegel S J, *Poly lactic-co-glicolic acid (PLGA) as biodegradable controlled drug delivery carrier. Polym* 3, 1377-1397, 2011).

As discussed above, the PLGA with an inherent viscosity less than 0.5 dL/g is degraded at a rate that is more suitable than that exhibited by other types of PLGA for the purpose of regenerating bone or cartilage. Therefore, the preferred type of PLGA of the present disclosure is a PLGA of an inherent viscosity below 0.5 dL/g.

"Inherent viscosity" refers to the measurement of the flow time of a polymer solution through a narrow capillary versus the flow time of pure solvent through the same capillary. This is a rheological method for determining the molecular weight of a polymer and is generally expressed in units of deciliters per gram.

Figure 1:
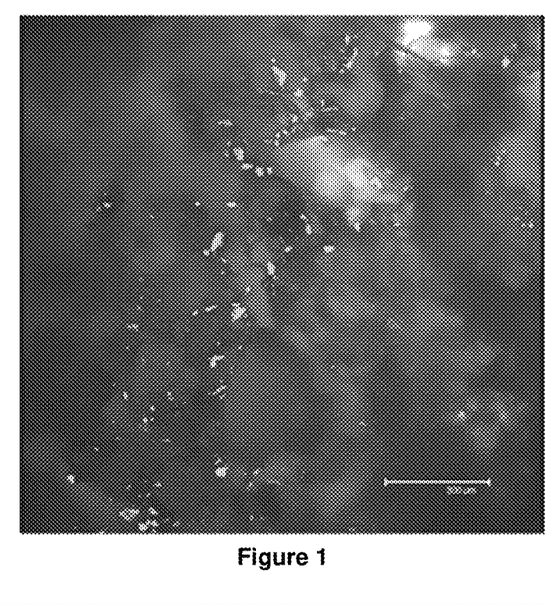
FIG. 1. Image by confocal microscopy of a scaffold prepared from PLGA, poly (ε-caprolactone) (PCL), starch and lysozyme labeled with fluorescein isothiocyanate (FITC) in 85:10:5 weight ratio.

The term "homogeneous matrix" refers to a matrix with spatial uniformity in its structure and uniformity in the composition thereof. In a homogeneous matrix, like that of the disclosure, there are no traces of the powder morphology of the starting materials as shown in the examples and in particular in Example 1 and FIG. 1. In FIG. 1 it can be seen that there is a uniform distribution of lysozyme, which is the biologically active substance used in the corresponding example.

Figure 2:
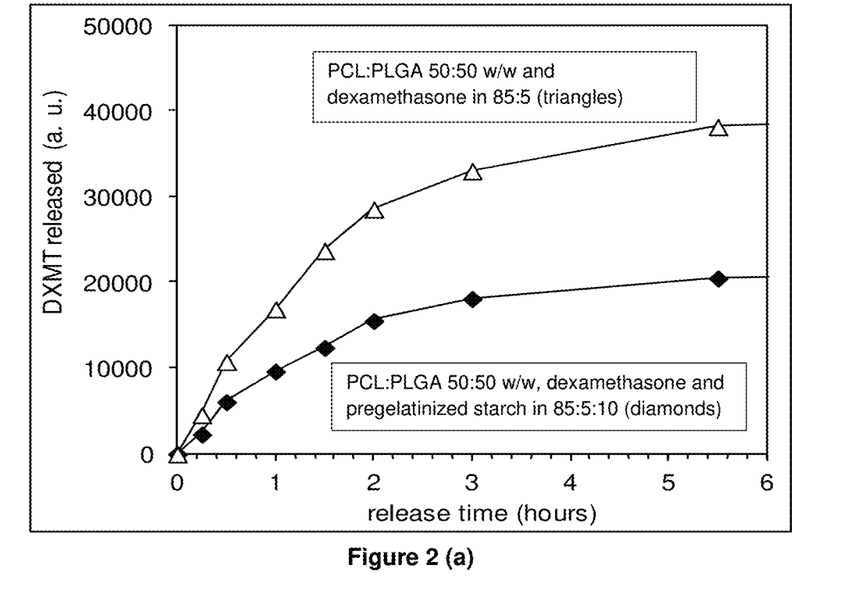
FIG. 2. Dexamethasone release profiles in phosphate buffer medium from matrices of 10 milligrams prepared from mixtures of (i) PCL:PLGA 50:50 w/w, dexamethasone and pregelatinized starch in 85:5:10 weight ratio (diamonds); (ii) PCL:PLGA 50:50 w/w and dexamethasone 85:5 (triangles). Release profiles at (a) 6 hours and (b) 3 weeks.

In a particular embodiment, the system of the disclosure further comprises a release-regulating compound selected from the group consisting of an oligosaccharide and a polysaccharide. The addition of a release-regulating compound to the system of the disclosure allows the modulation of the release profile of the active substance. In FIG. 2, the release profiles of dexamethasone when the system comprises starch and a system that does not comprise starch can be compared. It is noted that at short periods of time, less than 7 days, the released amount of the biologically active substance is half with respect to the system that does not comprise the polysaccharide. At longer periods of time, for example after 21 days, the released amount of active substance is similar for both systems.

The term "release-regulating compound" refers to the compound that modulates the release of biologically active substances in a formulation to obtain a suitable release profile in order for the therapeutic effect to be manifested.

In a particular embodiment of the disclosure, the release-regulating compound is starch or a starch derivative. "Starch derivative" is understood as an oligomer or polymer obtained from starch as a starting material by physical, chemical or enzymatic modification. In a particular embodiment of the disclosure, the release-regulating component is a starch derivative obtained through total or partial chemical modification by acylation, acetylation or oxidation by replacing part of the hydroxyl groups of the starch with acyl, acetyl or ether groups. Thus it is possible to increase the hydrophobicity and mechanical properties of starch.

Starch is a natural polysaccharide composed of a mixture of amylose and amylopectin, and some of their derivatives. In native state, starch is presented in the form of semicrystalline granules that cannot be easily mixed with synthetic polymers, such as PLGA (Mani R, Bhattacharya M, *Properties of injection moulded blends of starch and modified biodegradable polyesters. Eur Polym J* 37, 515-526, 2001; Wang N, Yu J, Chang P R, Ma X, *Influence of formamide and water on the properties of thermoplastic starch/poly(lactic acid) blends. Carbohydrate Polym* 71, 109-118, 2008). Furthermore, the incorporation of starch into the scaffolds can facilitate cell adhesion, proliferation and differentiation.

However, incorporation of an oligosaccharide or polysaccharide into the systems of the disclosure is hindered by the low compatibility between the oligosaccharide or polysaccharide, particularly starch, and PLGA. If the starch is pretreated before it is used, it is possible to improve the compatibility. Thus, in a particular embodiment, the release-regulating compound is pregelatinized starch.

In a particular embodiment of the disclosure, the proportion of the release-regulating compound is comprised between 0.1% and 25% by weight relative to PLGA with an inherent viscosity less than 0.5 dL/g.

Figure 4:
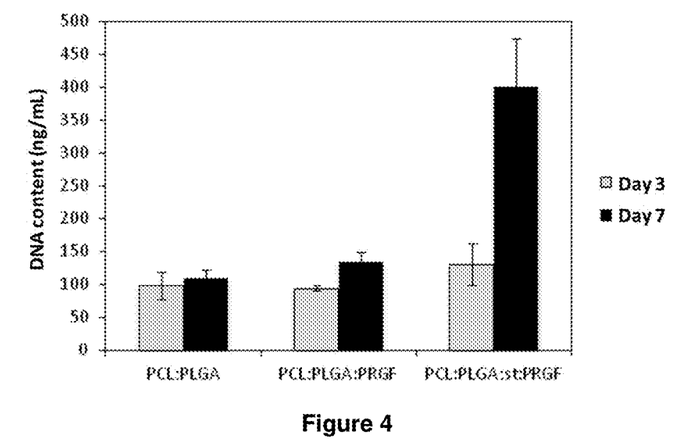
FIG. 4. 3 (grey bars) and 7 (black bars) days Quant-IT PicoGreen dsDNA proliferation assay of mesenchymal stem cells seeded on scaffolds of (a) PLGA (i.v. 0.2 dL/g) and PCL in 50:50 w/w ratio, (b) PLGA (i.v. 0.2 dL/g) and PCL in 50:50 w/w ratio and PRGF 5% relative to the weight of the PCL:PLGA mixture; and (c) PLGA (i.v. 0.2 dL/g) and PCL in 50:50 w/w ratio with pregelatinized starch at 90° C. (st) and PRGF at 10 and 5%, respectively, relative to the weight of the PCL:PLGA mixture.

Another advantage of the systems of the disclosure comprising starch is that they provide a greater degree of cell proliferation, as demonstrated in Example 3 and is illustrated in FIG. 4. In a preferred embodiment, the systems of the disclosure comprise pregelatinized starch.

In a particular embodiment, the systems of the disclosure as described above further comprise a synthetic or semisynthetic biodegradable polyester different from poly(D, L-lactic-co-glycolic acid) with inherent viscosity less than 0.5 dL/g. In a particular embodiment, the synthetic or semisynthetic polyester is selected from the group consisting of poly(D, L-lactic-co-glycolic acid) with inherent viscosity greater than 0.5 dL/g, poly(epsilon-caprolactone), poly(lactic acid), poly(glycolic acid), poly(butylensuccinate), poly(p-dioxanone), polycarbonate, polyhydroxybutyrate, and the copolymers thereof.

In a particular embodiment, in the systems of the disclosure as described above, the matrix further comprises a release-regulating component as described above and a biodegradable synthetic polyester different from the poly (D,L-lactic-co-glycolic acid) of an inherent viscosity less than 0.5 dL/g, as described above.

In a more particular embodiment, in the systems of the disclosure as described above, the matrix further comprises pregelatinized starch and poly(epsilon-caprolactone).

A preferred embodiment of the disclosure relates to a system for administering biologically active substances comprising a homogeneous and biodegradable matrix with a solid or semi-solid consistency having a porosity higher than 50%, said matrix comprises poly(D,L-lactic-co-glycolic acid) of an inherent viscosity less than 0.5 dL/g, at least one biologically active substance, a release-regulating compound selected from the group consisting of an oligosaccharide and a polysaccharide, and a synthetic or semisynthetic biodegradable polyester different from the poly(D,L-lactic-co-glycolic acid) of an inherent viscosity less than 0.5 dL/g.

In an even more preferred embodiment, the disclosure relates to a system for administering biologically active substances comprising a homogeneous and biodegradable matrix with a solid or semi-solid consistency having a porosity higher than 50%, said matrix comprises poly(D,L-lactic-co-glycolic acid) of an inherent viscosity less than 0.5 dL/g, at least one biologically active substance, pregelatinized starch and poly(epsilon-caprolactone).

In another particular embodiment, the systems of the disclosure further comprise a plasticizing agent. In a particular embodiment, the plasticizing agent is selected from water, glycerol, sorbitol, maltitol, xylitol, polyethylene glycol, formamide, urea, propylene glycol, triethylene glycol and fatty acids.

In a particular embodiment of the disclosure, the plasticizing agent is in a proportion of between 0.5 and 65% by weight with respect to the release-regulating component. The plasticizing agent improves the compatibility of the release-regulating compound with the PLGA.

The present disclosure also relates to a method for obtaining a system for administering biologically active substances comprising a homogeneous and biodegradable matrix with a solid or semi-solid consistency having a porosity higher than 50%, said matrix comprising poly(D,L-lactic-co-glycolic acid) and at least one biologically active substance, comprising:

a) preparing a physical mixture comprising poly(D,L-lactic-co-glycolic acid) and a biologically active substance and, optionally a porogenic agent;

b) heating the mixture at a temperature equal to or less than 40° C.;

c) placing the said mixture in contact with a compressed gas or supercritical fluid at a pressure between 40 and 120 bar and a temperature between 20 and 40° C. during a time period between 5 minutes and 24 hours; and d) depressurization at a rate between 2 and 8 bar/min with cooling through the addition of a compressed liquid at a temperature between −196 and 19° C., the liquid being gaseous at 25° C. and 1 atmosphere of pressure.

In a preferred embodiment, the poly(D,L-lactic-co-glycolic acid) used in stage a) of the method of the disclosure has an inherent viscosity less than 0.5 dL/g. The method of the disclosure is particularly designed for obtaining systems comprising a matrix based on PLGA with low inherent viscosity, in particular an inherent viscosity less than 0.5 dL/g, as it avoids the problems encountered in the state of the art for this material that loses its physical and mechanical integrity rendering it useless for its purpose as an implant or scaffold.

From the standpoint of processing, the use of the compressed gases and supercritical fluids technology has emerged as a viable, reproducible, and environment-friendly alternative to obtain scaffolds and components of scaffolds that are free from traces of solvents by applying moderate conditions of processing. The foaming techniques using $CO_2$ as a compressed gas or in supercritical conditions as a solute of a polymer, enables materials with controlled porosity and pore distribution to be obtained, in few stages, at a temperature compatible with thermosensitive components and without using organic solvents that can cause environmental problems and compromise the biocompatibility of the scaffold (De Ponti R, Lardini E, Martini A, Torricelli C, Use of supercritical fluids to obtain porous sponges of biodegradable polymers. WO1991009079 A1).

The method of the disclosure has the advantages of not requiring the incorporation of organic solvents or water in any of its stages, it is carried out in a single step, and the working temperatures are comprised between 20 and 40° C., which are compatible with the incorporation of heat-sensitive components such as biologically active substances, it also takes place under environment-friendly conditions, and overcomes the current limitations of use of polymers with low inherent viscosity such as PLGA with an inherent viscosity less than 0.5 dL/g.

The method of the disclosure is based on melting or heating the polymeric mixture above the glass transition temperature of PLGA, or of the polymeric mixture containing PLGA in the event there are any additional components as described above.

In stage a) of the method it is possible to add other compounds that are useful for the functionality of the obtained system. In a particular embodiment, the physical mixture of stage a) further comprises a release-regulating compound and/or a biodegradable synthetic polyester different from poly(D,L-lactic-co-glycolic acid) with an inherent viscosity less than 0.5 dL/g.

In a particular embodiment, the method as described above comprises an additional stage, before stage a), wherein the release-regulating compound is pregelatinized in an aqueous medium at a temperature between 70 and 140° C., cooled down and dried before being incorporated into the mixture in stage a).

In a particular embodiment of the disclosure, the starch has been pregelatinized in an aqueous medium at a temperature between 70 and 140° C., cooled and dried in an oven or by freeze drying or supercritical drying after a prior solvent exchange step.

The disclosure further provides a method for removing a porogenic agent with the proviso that the porogenic agent is selected from the group consisting of ammonium bicarbonate, ammonium carbonate, sodium bicarbonate and ammonium phosphate by thermal decomposition. Thus leaching stages such as lixiviation, which drags the biologically active substance present in the system, are avoided. Drying after lixiviation is not necessary either.

Thus, in a particular embodiment, the method as described above comprises an additional stage for the removal of the porogenic agent, with the proviso that the porogenic agent used in stage a) is selected from the group consisting of ammonium bicarbonate, ammonium carbonate, sodium bicarbonate and ammonium phosphate, comprising heating the material obtained in stage d) at a temperature between 20 and 50° C.

In a particular embodiment, the method as described above further comprises the formation of a scaffold in the form of a monolithic implant or a multiparticulate system.

In another particular embodiment, the proportion of poly (D,L-lactic-co-glycolic acid) with respect to the release-regulating compound is comprised between 75 and 99.9%.

The preparation of the physical mixture, according to stage a) of the method, can be performed using standard mixing techniques, such as a paddle mixer, a planetary mixer or Turbula-type shaker-mixer The application of a compressed gas or supercritical fluid as a processing medium, according to stage c) of the method of the disclosure, can be carried out, for example, by pressurizing a temperature-controlled autoclave with a compressor or a pump or introducing liquid $CO_2$ or dry ice in the said autoclave. At this stage, the biologically active substances can be found dissolved or suspended with respect to the polymeric mixture. In a particular embodiment, the contact time between the compressed gas or supercritical fluid and the mixture is between 5 minutes and 24 hours. In a more particular embodiment, it is between 15 minutes and 1 hour. In a preferred embodiment, it is between 20 minutes and 40 minutes.

The mixture of stage c) is depressurized and cooled sequentially or simultaneously to obtain the system of the disclosure described above with a solid or semi-solid consistency and homogenous appearance. Carbon dioxide interacts with the polymers acting as a plasticizer and swelling agent, thereby reducing the glass transition temperature and/or the melting temperature in the case of a mixture containing a biodegradable synthetic polyester. The amount of carbon dioxide absorbed during the processing and consequent swelling of the polymer mixture is proportional to the temperature and pressure of the processing medium. During the removal of $CO_2$ there exists a thermodynamic instability that causes the formation of void volume (porosity) by nucleation. When $CO_2$ leaves the matrix, the melting temperature or the glass transition temperature increases above the working temperature and the scaffold is vitrified. During depressurization, as in stage d), under ambient conditions, the degassing or depressurization rate influences the pore size and interconnectivity of the final scaffold. The cooling rate during depressurization also influences the pore size and interconnectivity of the final scaffold.

The resistance to expansion of the pores after nucleation is very low for polymer matrices with components with low inherent viscosity (<0.5 dL/g), forming very large pores (greater than one millimeter). In this particular embodiment, after partial depressurization, cold compressed liquid is added to cool down the sample, to reduce the viscosity of the mixture due to temperature drop, and to regulate the expansion of the pores. Said compressed liquid must be gaseous at ambient pressure and temperature. The liquid $CO_2$ or liquid $N_2$ is preferably used.

In a particular embodiment, a solid porogenic agent is incorporated into the matrix before the mixing stage. In a more particular embodiment, said porogenic agent is thermally decomposed through a post-processing stage by heating the material at a temperature comprised between 20 and 50° C. In a preferred embodiment, the porogenic agent is ammonium bicarbonate. In a particular embodiment of the disclosure, the proportion of porogenic agent is comprised between 15% and 65% by weight with respect to the biocompatible polymer material.

In another aspect, the disclosure is also aimed at the system for administering biologically active substances obtained by the method as described above.

By implementing the method of the disclosure, systems with a porosity greater than 50% (see examples) are obtained, which is a convenient porosity in implants for bone regeneration considering that implants for bone regeneration have to be able to emulate the bone morphology. It is therefore favorable to use a matrix with textural properties suitable for facilitating the entry, adhesion and proliferation of cells as well as the neovascularization and diffusion of gases and nutrients to cells. Thus, it is convenient to use, therefore, a matrix with a porosity analogous to the trabecular bone of between 50 and 90%, preferably close to its upper value (Karageorgiou V, Kaplan D, *Porosity of 3D biomaterial scaffolds and osteogenesis, Biomater.* 2006, 26, 5474-5491) (Rezvan K, Chen Q Z, Blaker J J, Boccaccini A R, *Biodegradable and bioactive porous polymer/inorganic composite scaffolds for bone tissue engineering, Biomater.* 2006, 27, 3413-3431).

As a result of the method of the disclosure, systems with concave pores (see examples) are obtained. This pore geometry is suitable for the application of the systems of the disclosure to tissue regeneration since it favors growth (Zadpoor A A, *Bone tissue regeneration: the role of scaffold geometry, Biomater. Sci.,* 2015, 3, 231-245).

Systems obtainable by the method of the disclosure have pores with a uniform wall thickness and substantially thinner than the pore size.

The present disclosure uses a processing medium in conditions of compressed gas or supercritical fluid. A fluid is in supercritical conditions when its pressure and temperature are above its critical point and is characterized by intermediate properties between a liquid and a gas. Examples of fluids that can be used with this disclosure are selected from carbon dioxide ($CO_2$), water, nitrous oxide, methane, ethane, ethylene, propane, pentane, benzene, methanol, ethanol, isopropanol, various fluorocarbons such as chlorotrifluoromethane and monofluoromethane, toluene, pyridine, cyclohexane, decalin, cyclohexanol, o-xylene and tetralin. The present disclosure contemplates the use of these substances individually or in combination, as well as the use of additives. In a particular embodiment of the disclosure, the compressed gas or supercritical fluid is $CO_2$. The individual use of $CO_2$ as a processing medium is preferred because of its non-flammability, low cost and easy removal from the medium at ambient temperature and pressure. There will be, therefore, no residual $CO_2$ in the final product which can contribute to problems in the use thereof.

The term "biologically active substance" refers to any substance that alters, promotes, accelerates, prolongs, inhibits, activates or at least affects the biological or chemical processes occurring in humans and animals. When one or more biologically active substances are incorporated into the system of the disclosure, they are dispersed at the molecular or particle level. The system is suitable for incorporating biologically active substances regardless of the solubility characteristics thereof. Because the characteristics of the system components and processing conditions, itis especially suitable for incorporating thermosensitive biologically active substances.

In a particular embodiment, the systems of the disclosure may further comprise another biologically active substance.

In a particular embodiment, the biologically active substances are selected from hormones, anti-inflammatory drugs, antineoplastic drugs, antimicrobial agents and morphogenic substances for bone defect repair and other applications in regenerative medicine. In a more particular embodiment, the biologically active substance is a mixture of growth factors contained in platelet rich preparation (PRGF). In another particular embodiment, the biologically active substance is a preparation rich in growth factors. This preparation is designed to promote the regulation of cell interactions with one another and with the extracellular matrix in soft tissues and bones.

In another particular embodiment, the proportion of biologically active substance is comprised between 0.1 and 15% by weight with respect to poly(D,L-lactic-co-glycolic acid).

In a particular embodiment, the disclosure relates to an additional stage to the method described, which comprises forming implants: the cooled system can be divided in portions by cutting. In an even more particular embodiment, the removal of a thin, dense and non-porous outer film may be necessary before being used for implant purposes.

The systems obtained, in the form of particles or with another suitable morphology for implantation, are suitable as implants capable of providing release profiles of biologically active substances that are tuned to specific requirements.

In a preferred embodiment, the disclosure is aimed at the use of a system as defined above in the preparation of an implant capable of releasing a biologically active substance for bone defect repair.

In another aspect, the disclosure relates to an implant comprising a system as described above.

In another aspect, the disclosure relates to a scaffold comprising a system as described above.

In another aspect, the disclosure relates to the use of the systems of the disclosure described above, the implant of the disclosure or the scaffold of the disclosure for the production of a medicament.

In a particular embodiment, the medicament is for the treatment of pathological or physiological states in humans or animals.

In a particular embodiment, the medicament is for bone regeneration.

In a particular embodiment, the medicament is for cartilage regeneration.

Next, for a better understanding of the disclosure, the following examples are provided, without these implying a limitation to the disclosure.

Example 1

Preparation of Matrices of PLGA/PCL with Starch and Lysozyme

Mixtures of PLGA (i.v. 0.2 dL/g) and PCL in 50:50 w/w ratios were prepared and lysozyme labelled with FITC and pregelatinized starch were incorporated at 90° C. and dried in an oven at 5 and 10% relative to the weight of the PCL:PLGA mixture, respectively, in a Turbula-type shaker-mixer (WAB AG Maschinenfabrik, T2C, Switzerland). Said mixture was processed in the form of tablets of 400 mg using an eccentric tablet press machine (Erweka Apparatebau, E KOW, Frankfurt, Germany). Said mixture was put in contact with compressed $CO_2$ medium at 60 bar and ambient temperature (21° C.) in an autoclave (100 mL, TharSFE) for 30 min. Thereafter, the $CO_2$ was depressurized to atmospheric pressure at a rate of 5 bar/min with three periodic additions of 10-15 g of liquid $CO_2$ at 1° C. and 60 bar. The non-porous outer film of the scaffold was removed with a scalpel and the characterization of said scaffold was carried out.

The obtained scaffold has a porosity of 75% by helium pycnometry and pores with high curvature and concave surface, wall thicknesses of 10-20 microns and a mean pore size of around 50 microns according to SEM microscopy. The picture by confocal microscopy (FIG. 1) of the cross-section of the scaffold shows a homogeneous distribution of the lysozyme within said scaffold (intense white regions in the picture).

Example 2

Preparation of Matrices of PLGA/PCL with Starch and Dexamethasone Release Assays Two mixtures of: (a) PLGA (i.v. 0.2 dL/g) and PCL in 50:50 w/w ratios with dexamethasone at 5% relative to the weight of the PCL:PLGA mixture and (b) PLGA (i.v. 0.2 dL/g) and PCL in 50:50 w/w ratios with dexamethasone and pregelatinized starch at 120° C. and dried at 5 and 10% relative to the weight of the PCL:PLGA mixture, respectively, were prepared in a Turbula-type shaker-mixer (WAB AG Maschinenfabrik, T2C, Switzerland). Said mixtures were processed in the form of tablets of 400 mg using an eccentric tablet press machine (Erweka Apparatebau, E KOW, Frankfurt, Germany). Said mixtures were put in contact with compressed $CO_2$ medium at 60 bar and ambient temperature (27° C.) in an autoclave (100 mL, TharSFE) for 30 min. Thereafter, the $CO_2$ was depressurized to atmospheric pressure at a rate of 5 bar/min with three periodic additions of 10-15 g of liquid $CO_2$ at 1° C. and 60 bar. The non-porous outer film of the scaffolds was removed with a scalpel and the characterization of said scaffolds was carried out.

The obtained scaffolds have a porosity of 75-85% by helium pycnometry and pores with high curvature and concave surface, wall thicknesses of 10-20 microns and a mean pore size of around 50 microns according to SEM microscopy.

To carry out the release assay, 10 mg portions of scaffold pieces were immersed in 50 mL of phosphate buffer pH 7.4 and the system was constantly stirred at 60 rpm and 37° C. The amount of dexamethasone released was monitored by measuring its concentration in the release medium by HPLC at a wavelength of 242 nm. The obtained release profiles are showed in FIG. 2. The scaffolds led to a sustained release during, at least 21 days (FIG. 2a), it being possible to see slower releases at short time periods in the case of the sample containing starch (FIG. 2b).

Example 3

Preparation of Matrices of PCL:PLGA:Starch with PRGF, and Cytotoxicity and Cell Proliferation Assays Three mixtures of: (a) PLGA (i.v. 0.2 dL/g) and PCL in 50:50 w/w ratios, (b) PLGA (i.v. 0.2 dL/g) and PCL in 50:50 w/w ratios with preparation rich in growth factors (PRGF) at 5% relative to the weight of the PCL:PLGA mixture, obtained by centrifugation methods (400 g, 15 min) and freeze-thaw cycles (4 cycles) followed by separation by centrifugation (14800 g, 4° C., 10 min) and lyophilization (−80° C.) from blood donations by the buffy-coat method (supplier Centro de Transfusión de Galicia); and (c) PLGA (i.v. 0.2 dL/g) and PCL in 50:50 w/w ratios with pregelatinized starch at 90° C. at 10% relative to the weight of the PCL:PLGA mixture and PRGF at 5% relative to the weight of the PCL:PLGA mixture, were prepared in a Turbula-type shaker-mixer (WAB AG Maschinenfabrik, T2C, Switzerland). Said mixtures were processed in the form of tablets of 400 mg using an eccentric tablet press machine (Erweka Apparatebau, E KOW, Frankfurt, Germany). Said mixtures were put in contact with compressed $CO_2$ medium at 60 bar and 25° C. in an autoclave (100 mL, TharSFE) for 30 min. Thereafter, the $CO_2$ was depressurized to atmospheric pressure at a rate of 5 bar/min with three periodic additions of 10-15 g of liquid $CO_2$ at 1° C. and 60 bar. The non-porous outer film of the scaffolds was removed with a scalpel and the characterization of said scaffolds was carried out.

The obtained scaffolds have a porosity of 75-85% by helium pycnometry and pores with high curvature and concave surface, wall thicknesses of 10-20 microns and a mean pore size of around 50 microns according to SEM microscopy.

Figure 3:
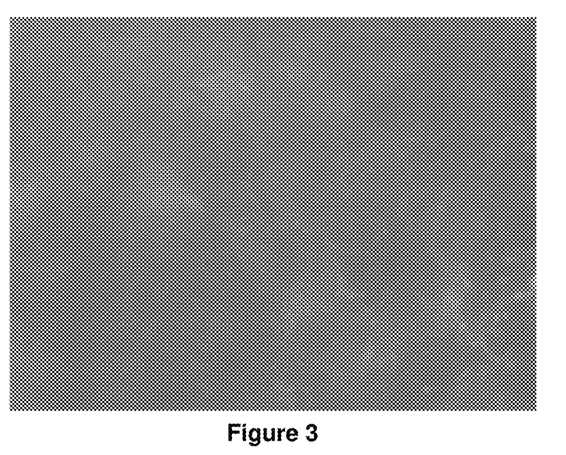
FIG. 3. 7 days Cytotoxicity assay of scaffolds of PCL, PLGA, starch and PRGF in 42.5:42.5:5:10 weight ratio by seeding mesenchymal stem cells. Living cells are stained with calcein green (grey in the figure) and dead cells with propidium iodide (red color, absent in the figure).

To analyze the cytotoxicity of the scaffolds, a LIVE/DEAD® assay (Molecular Probes; USA) was carried out, including the staining with calcein (green colour; 1 mg/mL) and propidium iodide (red colour; 1 mg/mL) in PBS (pH 7.4; ratio 1:1:98) of live and dead cells, respectively. For this, 20,000 mesenchymal cells were seeded over each scaffold (5×5×5 mm) and cultivated for 7 days in an incubator. Then, the scaffolds were washed with PBS and 100 μL of the stain were added and were incubated for 10 minutes in darkness. Finally, the citotoxicity of the scaffolds was evaluated from images of the scaffolds obtained by confocal microscopy (LCS, Leica Microsystems, Germany). FIG. 3 shows the results from the LIVE/DEAD® citotoxicity assay of the sample (c) following the protocol of the supplier with green stain (grey in the figure) indicating the viability of live mesenchymal stem cells in about 100% of the cases.

FIG. 4 shows the proliferation assay of mesenchymal stem cells evaluated by quantification of DNA using the protocol of the commercial kit Quant-IT PicoGreen dsDNA (Life Technologies; USA). For this, 20,000 mesenchymal cells were seeded over each scaffold (5×5×5 mm) and cultivated for 3 and 7 days in an incubator at 37° C. and 5% of $CO_2$. Then, the scaffolds were washed with PBS and placed in test tubes of 2.5 mL (Eppendorf, Germany) and 1 mL of ultrapure water was added. The samples were subjected to 3 freeze-thaw cycles and, then, sonicated during 5 min and then homogenized in a vortex. Finally, an assay for the quantification of DNA was carried out following the instructions of the manufacturer and the results were evaluated based on the absorbance read in a spectrofluorimeter Fluostar Optima (BMG Labtech, Germany). After 7 days of seeding, a higher DNA concentration was observed in the sample containing starch and PRGF (sample (c)) than in the sample without starch (sample (b)) and than in the sample with neither starch nor PRGF (sample (a)) indicating a higher extent of cell proliferation for sample (c) during this time period.

Example 4

Preparation of Matrices of PLGA and PLGA:PCL with Macroporosity Generated by Thermal Decomposition of Ammonium Bicarbonate Five mixtures of: a) PLGA (i.v. 0.2 dL/g) and ammonium bicarbonate in 50:50 w/w ratios; b) PLGA (i.v. 0.2 dL/g) and PCL in 50:50 w/w ratios and ammonium bicarbonate in 50:50 w/w ratios; c) PLGA (i.v. 0.2 dL/g) and PCL in 50:50 w/w ratios; d) PLGA (i.v. 0.2 dL/g) and PCL in 50:50 w/w ratios, pregelatinized starch at 120° C. and ammonium bicarbonate in 45:5:50 w/w ratios; and (e) PLGA (i.v. 0.2 dL/g) and PCL in 50:50 w/w ratios, pregelatinized starch at 120° C. in 85:10 w/w ratios, were prepared. Said mixtures were processed in a Turbula-type shaker-mixer (WAB AG Maschinenfabrik, T2C, Switzerland) and shaped in the form of tablets of 400 mg using an eccentric tablet press machine (Erweka Apparatebau, E KOW, Frankfurt, Germany). Said mixtures were put in contact with compressed $CO_2$ medium at 60 bar and 27° C. in an autoclave (100 mL, TharSFE) for 30 min. Thereafter, the $CO_2$ was depressurized to atmospheric pressure at a rate of 5 bar/min with three periodic additions of 10-15 g of liquid $CO_2$ at 1° C. and 60 bar. The non-porous outer film of the scaffolds was removed with a scalpel and the characterization of said scaffolds was carried out. The obtained scaffold was left in the air at 37° C. during 24 hours for the thermal decomposition of the porogenic salt.

Figure 5:
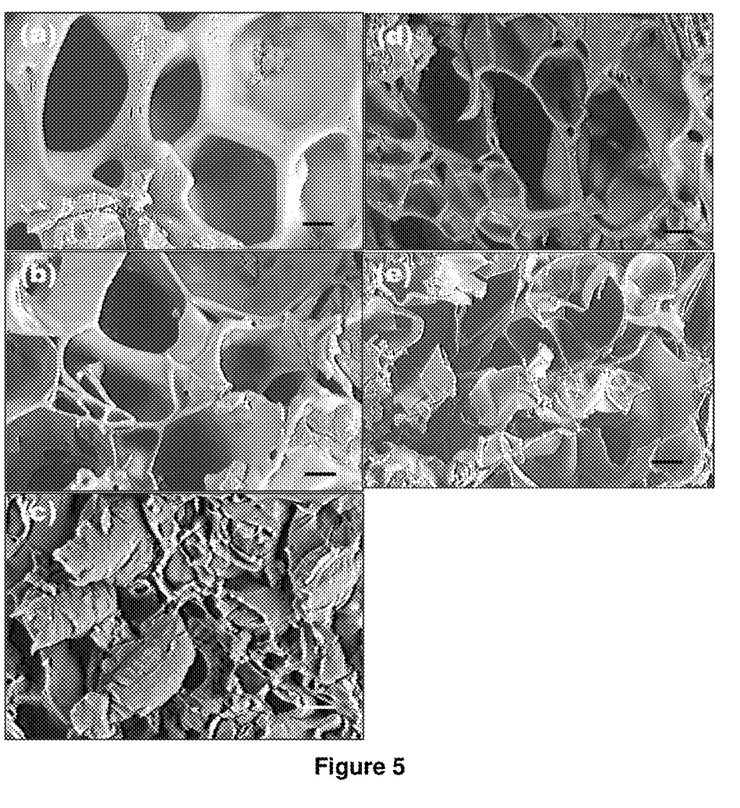
FIG. 5. SEM image of a dual porosity scaffold prepared from (a) mixtures of PLGA (i.v. 0.2 dL/g) and a porogenic agent (ammonium bicarbonate) in a weight ratio of 50:50; (b) mixtures of PCL:PLGA 50:50 w/w and a porogenic agent (ammonium bicarbonate) in weight ratio 50:50; (c) mixtures of PCL:PLGA 50:50 w/w; (d) mixtures of PLGA (i.v. 0.2 dL/g) and PCL in 50:50 w/w ratio, pregelatinized starch at 120° C. and ammonium bicarbonate in weight ratio of 45:5:50; and (e) mixtures of PLGA (i.v. 0.2 dL/g) and PCL in 50:50 w/w ratio, and pregelatinized starch at 120° C. in weight ratio 85:10. Scale bar: 50 μm.

The images by SEM microscopy of the obtained scaffolds are shown (FIG. 5). Structural homogeneity of the material can be seen in all the cases without presence of the powder morphology of the starting materials, without the presence of microspheres or nanoparticles, and without the presence of necks or grain boundaries in the pores. The obtained scaffolds have a porosity of 70-80% by helium pycnometry. FIGS. 5a and 5b show the images by SEM microscopy of scaffolds with dual porosity prepared from mixtures of PLGA and a porogenic agent (ammonium bicarbonate) in 50:50 w/w ratio (FIG. 5a) and of PCL:PLGA 50:50 w/w and a porogenic agent (ammonium bicarbonate) in 50:50 w/w ratio after the removal of the porogenic agent (FIG. 5b). Remains of the ammonium bicarbonate were not observed in the porous structures and weight losses of 50% were obtained (corresponding to the removal of the salt). The obtained pores are of high curvature with concave surface and wall thicknesses of 10-30 microns. The resulting porous structure is of the dual type according to SEM microscopy: pores of 50 microns formed by supercritical foaming and of 100-300 microns formed by thermal decomposition of the porogenic agent. For the sake of comparison, FIG. 5c shows the image of a scaffold prepared from PCL:PLGA 50:50 w/w mixtures. In this case, a family of pores mainly of 50 microns, of high curvature with concave surface and wall thicknesses of 10-20 microns is observed.

FIG. 5d shows the image by SEM microscopy of a scaffold with dual porosity prepared from PCL:PLGA 50:50 w/w mixtures, pregelatinized starch at 120° C. and a porogenic agent (ammonium bicarbonate) in 45:5:50 w/w ratio after removal of the porogenic agent. Remains of the ammonium bicarbonate were not observed in the porous structure and weight losses of 50% were obtained (corresponding to the removal of the salt). The obtained pores are of high curvature with concave surface and wall thicknesses of 15-25 microns. The resulting porous structure is of the dual type according to SEM microscopy: pores of 50 microns formed by supercritical foaming and of 100-300 microns formed by thermal decomposition of the porogenic agent. For the sake of comparison, FIG. 5e shows the image of a scaffold prepared from PCL:PLGA 50:50 w/w mixtures, pregelatinized starch at 120° C. in 85:10 w/w ratios. In this case, a family of pores mainly of 50 microns of high curvature with concave surface and wall thicknesses of 10-20 microns is observed.

Example 5

Preparation of Matrices of PCL:PLGA:Starch Pregelatined and Dried Through Different Techniques with PRGF, Protein Release Tests Three mixtures of: (a) PLGA (i.v. 0.2 dL/g) and PCL in 50:50 w/w ratio with preparation rich in growth factors (PRGF) at 5% relative to the weight of the PCL:PLGA mixture, obtained by methods of centrifugation (400 g, 15 min) and freeze-thaw cycles (4 cycles) followed by separation by centrifugation (14800 g, 4° C., 10 min) and lyophilized (−80° C.) from blood donations by the buffy-coat method (supplier Centro de Transfusión de Galicia); (b) PLGA (i.v. 0.2 dL/g) and PCL in 50:50 w/w ratios with pregelatinized starch at 90° C. and oven-dried at 80° C. for 1 day at 10% relative to the weight of the PCL:PLGA mixture and PRGF at 5% relative to the weight of the PCL:PLGA mixture; and (c) PLGA (i.v. 0.2 dL/g) and PCL in 50:50 ratio with pregelatinized starch at 90° C. and lyophilized (LyoQuest Plus −85° C./ECO, Telstar; Spain) at 10% relative to the weight of the PCL:PLGA mixture and PRGF at 5% relative to the weight of the PCL:PLGA mixture, in a Turbula-type mixer (WAB AG Maschinenfabrik, T2C, Switzerland) were prepared. Said mixtures were processed in the form of tablets of 400 mg using an eccentric tablet press machine (Erweka Apparatebau, E KOW, Frankfurt, Germany).

Said mixtures were put in contact with compressed $CO_2$ at 60 bar and 27° C. in an autoclave (100 mL, TharSFE) for 30 min by placing the tablets in a rotating basket at 700 rpm. Thereafter, the $CO_2$ was depressurized until atmospheric pressure at a rate of 5 bar/min with three periodic additions of 10-15 g of liquid $CO_2$ at 1° C. and 60 bar. The non-porous outer film of the scaffolds was removed with a scalpel to proceed with the characterization of the said scaffolds.

The scaffoldsobtained have a volume 2.5-3.0 times the initial volume of the tablet as measured and compared from the initial and final dimensions, with a porosity of 60-85% by helium pycnometry and pores with high curvature and concave surface, wall thicknesses of 10-20 microns and a mean pore size of around 50-200 microns according to SEM microscopy.

Figure 6:
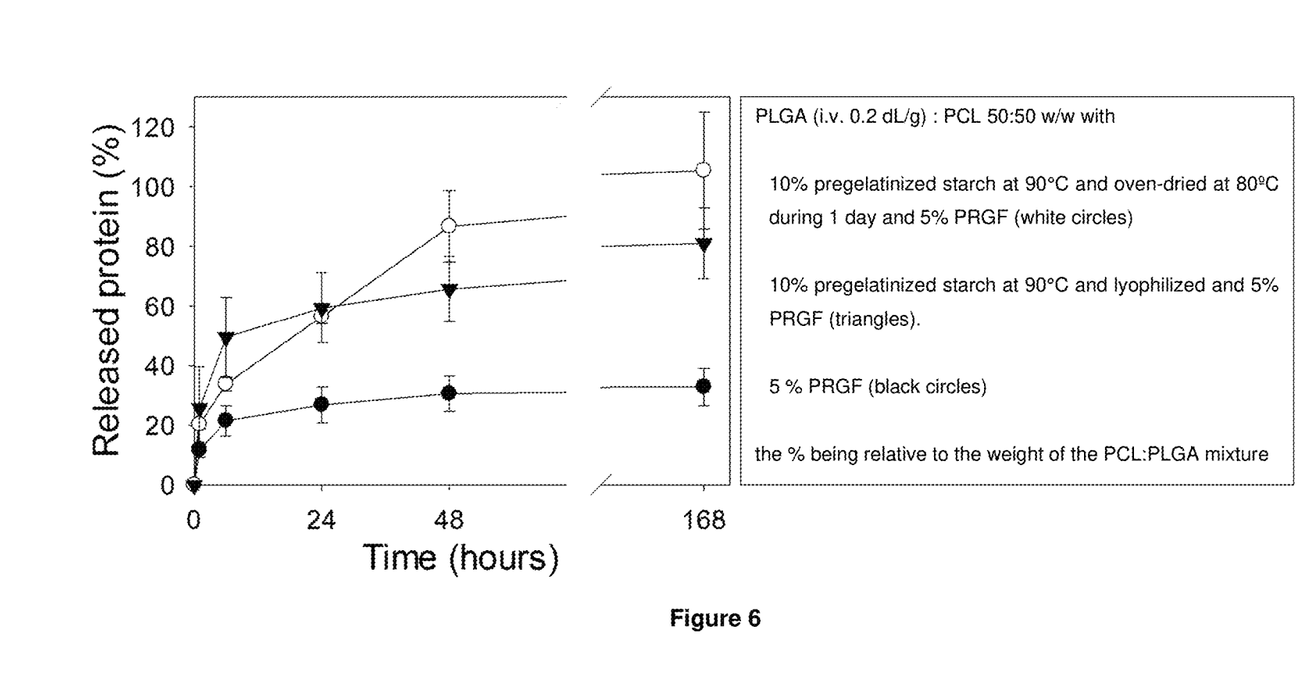
FIG. 6. Release profiles of rich in growth factors preparation in phosphate buffer medium of cubic matrices of 5 mm side prepared from mixtures of (i) PLGA (i.v. 0.2 dL/g) and PCL in proportions 50:50 w/w and PRGF at 5% relative to the weight of the PCL:PLGA mixture (black circles); (ii) PLGA (i.v. 0.2 dL/g) and PCL in proportions 50:50 w/w with pregelatinized starch at 90° C. and oven-dried at 80° C. during 1 day and PRGF at 10 and 5%, respectively, relative to the weight of the PCL:PLGA mixture (white circles); and (iii) PLGA (i.v. 0.2 dL/g) and PCL in proportions 50:50 w/w with pregelatinized starch at 90° C. and lyophilized and PRGF at 10 and 5%, respectively, relative to the weight of the PCL:PLGA mixture (triangles).

To carry out the release assay of the preparation rich in growth factors (PRGF), cubic pieces of 5 mm side from the scaffold were immersed in 50 mL of phosphate buffer pH 7.4 and the system was kept under agitation at 30 rpm and 37° C. The amount of protein released was monitored by measuring its concentration in the release medium by the bicinchoninic acid assay (BCA assay, Pierce ThermoSci, USA). The obtained release profiles are showed in FIG. 6. Scaffolds had a release profile in two steps: a first step of fast release of growth factors during the first 6 hours of release, followed by a second step with a more prolonged release during at least 7 days. The influence of the presence of modified starches (oven-dried or lyophilized) in the release of the growth factors during this second step can be appreciated by the sustained but faster release profile than for the sample not containing starch.

The invention claimed is:

1. A system for administering biologically active substances comprising a homogeneous biodegradable matrix with a solid or a semi-solid consistency having a porosity higher than 50% and less than or equal to 85%, said matrix comprises poly(D,L-lactic-co-glycolic acid), wherein said poly(D,L-lactic-co-glycolic acid) has an inherent viscosity less than 0.5 dL/g, pregelatinized starch at a proportion comprised between 0.1% and 25% by weight relative to said poly(D,L-lactic-co-glycolic acid), and poly(epsilon-caprolactone), and at least one biologically active substance selected from hormones, anti-inflammatory drugs, and morphogenic substances for bone defect repair, wherein said at least one biologically active substance is comprised at a proportion between 0.1 and 15% by weight with respect to poly(D,L-lactic-co-glycolic acid), wherein the poly(D,L-lactic-co-glycolic acid) and poly(epsilon-caprolactone) are present in 50:50 w/w ratios,
- wherein the system for administering biologically active substances is obtained by a method including the following steps:
  - a) preparing a physical mixture comprising poly(D,L-lactic-co-glycolic acid) and a biologically active substance and, optionally a porogenic agent,
  - b) heating the mixture at a temperature equal to or less than 40° C.,
  - c) placing the mixture in contact with a compressed gas or supercritical fluid at a pressure between 40 bar and 120 bar and a temperature between 20° C. and 40° C. during a time period between 5 minutes and 24 hours, and
  - d) depressurization at a rate between 2 bar/min and 8 bar/min with cooling through the addition of a compressed liquid at a temperature between −196° C. and 19° C., the liquid being gaseous at 25° C. and 1 atmosphere of pressure.

2. A method of treating bone defects, reparing bone defects, and/or regenerating bone or cartilage in humans or animals comprising administering a pharmaceutical effective amount of a system as defined in claim 1.

* * * * *